United States Patent

Manning et al.

[11] Patent Number: 5,993,853
[45] Date of Patent: Nov. 30, 1999

[54] DIETARY SUPPLEMENT

[76] Inventors: Bethany M. Manning; Thomas M. D. Manning; Rebecca A. Kaake; Gregory A. Kaake, all of 2455 S. Term St., Burton, Mich. 48519

[21] Appl. No.: 09/100,938

[22] Filed: Jun. 22, 1998

[51] Int. Cl.$^6$ ................... A61K 9/16; A61K 9/48
[52] U.S. Cl. .................... 424/456; 424/451; 424/489; 514/962
[58] Field of Search ................. 424/489, 456, 424/451; 514/962

[56] References Cited

U.S. PATENT DOCUMENTS

| | | | |
|---|---|---|---|
| 1,197,442 | 9/1916 | Burke | 426/319 |
| 1,717,920 | 6/1929 | Gilbert | 426/14 |
| 3,713,843 | 1/1973 | Pour-el et al. | 99/79 |
| 3,988,483 | 10/1976 | Deyoe et al. | 426/53 |
| 4,076,844 | 2/1978 | Ebner et al. | 426/17 |
| 4,313,960 | 2/1982 | Campagne | 426/17 |
| 4,477,481 | 10/1984 | Eisenhardt, Jr. et al. | 426/590 |
| 5,118,517 | 6/1992 | Palermiti | 426/443 |
| 5,616,355 | 4/1997 | Haast et al. | 426/384 |

*Primary Examiner*—James M. Spear
*Attorney, Agent, or Firm*—Richard C. Litman

[57] ABSTRACT

A dietary supplement comprising a reaction product of sodium bicarbonate and apple cider vinegar which is lyophilized.

10 Claims, No Drawings

DIETARY SUPPLEMENT

BACKGROUND OF THE INVENTION

1. Field of the Invention

The present invention relates generally to a dietary supplement. More specifically, the product is a lyophilized or freeze-dried reaction product of aqueous solutions of sodium bicarbonate and apple cider vinegar.

2. Description of the Related Art

The related art of interest is directed to various food supplements which contain added vitamins and minerals which add to the overall cost of preparation and purchase. There is a need for an inexpensive food supplement based on simple and inexpensive ingredients which still provides substantial health benefits to the health and vigor of the individual taking this food product. The related art will be discussed in order of perceived relevance to the present invention.

U.S. Pat. No. 4,477,481 issued on Oct. 16, 1984, to William A. Eisenhardt, Jr. et al. describes a method for producing dried citrus pulp by adding calcium and/or potassium oxide salts to fresh citrus pulp to raise the pH to at least 4.0. The lemon or orange pulp is frozen by liquid nitrogen and freeze-dried al less than 250 microns of mercury pressure, then in Example 1, using a shelf temperature profile of −20° C. for 20 hours, −15° C. for 8 hrs. and up to ambient temperature over a weekend period. The dried pulp is reconstituted in aqueous solution. The product is distinguishable for its reliance on a citrus pulp.

U.S. Pat. No. 1,717,920 issued on Jun. 18, 1929, to Valentine Gilbert describes a process of producing a low alcohol beverage from a 2–3.5% alcohol containing beer which is a malted cereal grain (barley) flavored with hops and brewed by slow fermentation with lactic acid bacteria. The acid content is lowered by adding sodium bicarbonate and optionally carbon dioxide under pressure. The product contains living lactic acid bacteria. The product is distinguishable for being beer and containing living bacteria.

U.S. Pat. No. 5,616,355 issued on Apr. 1, 1997, to William E. Haast et al. describes lyophilized granola-type health food products from apple juice and a mixture of 20% wheat bran and 80% oat bran having a high fiber content from 20–60 wt. % The mixture is shaped, frozen and lyophilized. The product is distinguishable for the required ingredient of bran solids.

U.S. Pat. No. 4,076,844 issued on Feb. 28, 1978, to Heinrich Ebner et al. describes two- and three-stage processes for the production of vinegar with high acetic acid concentration. For a two-stage process, a submerged vinegar fermentation is begun with ethanol added to establish a concentration of 1–5. When the acetic acid concentration reaches 13–15%, 20–50% of the liquid is discharged into a second fermentation tank. The first fermentation tank is resupplied with mash containing 2.5–10% ethanol, 1–6% acetic acid and 1–3 kgm. nutrients per 1 kiloliter solution for the bacteria resulting in a concentration of 7–10% acetic acid. Under aeration at constant temperature, up to 0.4% ethanol and greater than 15% acetic acid containing solution is obtained and removed from the second fermentation tank. This combined batch and continuous process is distinguishable for its reliance only on fermentation of vinegar from unknown vinegar sources.

U.S. Pat. No. 4,313,960, issued to Constant J. V. L. Compagne describes a preparation of concentrated natural vinegar obtained from a natural anaerobic fermentation of potato starch with Clostridium butylicum. The starting product solution contained acetone, 1.8 wt. % butanol and 0.22 wt. % ethanol. To 5 parts by volume of this acetone and alcohol solution, 1 part by volume natural vinegar having an acetic acid content of 12 wt. % and an ethanol content of 0.25 wt. % was added, and the solution reduced in volume 7% by freeze drying and contact with a sulfonated polymer ion exchange resin of divinylbenzene and styrene to add sodium chloride and to cause a separation of ethyl and butyl acetates. The resulting mixture is stored for 2 to 5 days to produce a concentrated natural vinegar containing ethyl acetate in a concentration of ethyl acetate to acetic acid of at least 1:150 ratio by weight. The product is distinguishable for the requirement for an ion exchange step of a potato derived extract.

U.S. Pat. No. 5,118,517 issued on Jun. 2, 1992, to Frank M. Palermiti describes a method of manufacturing powdered citrus fruit juice using dextran (molecular weight range of 10,000 to 40,000,000) as a drying agent which upon hydrolysis yields only glucose. The amount of dextran dissolved ranges from one-tenth to equal parts by weight of the total carbohydrate content of the fruit juice. The powder is distinguishable for its limitation to citrus fruits and the addition of dextran.

U.S. Pat. No. 1,197,442 issued on Sep. 5, 1916, to Charles E. Burke et al. describes the preservation of citrus fruit juices such as those of lemons, grapefruit and oranges by adding the white pith of that citrus fruit during a grating step. 0.15 wt. % of sulfur dioxide is added to the grated mixture of juice, pulp and white pith. The sponge mass is pressed and the previously filtered juice is added to the pressed spongy mass and the extracted juice. 0.12 to 1 wt. % of carbonate or acetate salts of calcium or magnesium are added to the mixture to coagulate the pulp to a spongy mass at 25–35° C. for 10 to 24 hours. The juice is separated by filtration, pasteurized at 55° to 60° C. and bottled. The juice preservation process is distinguishable for the additions of the citrus fruit pith and sulfur dioxide.

U.S. Pat. No. 3,713,843 issued on Jan. 30, 1973 to Akiva Pour-el et al. describes a freeze-dried soybean protein powder to be included in carbonated or non-carbonated acidic beverages, e.g., orange drink. Hydrochloric and phosphoric acids are added during the solubilizing process with an acid fungal proteinase enzyme to maintain the pH at 2.7 to 4.75. The soybean powder extract is distinguishable for its protein value and the use of an enzyme.

None of the above inventions and patents, taken either singularly or in combination, is seen to describe the instant invention as claimed. Thus, a dietary supplement solving the aforementioned problems is desired.

SUMMARY OF THE INVENTION

The reaction product of sodium bicarbonate and raw apple cider vinegar in aqueous is subjected to lyophilization or freeze-drying for at least 24 hours to obtain a fine beige-colored powder which is packaged in gelatin capsules for human consumption. The process is economical and utilizes two economical ingredients to obtain a product which has been shown to improve digestion, to rid impurities in the blood and to relieve arthritic pain in humans.

Accordingly, it is a principal object of the invention to provide a dietary supplement for human consumption.

It is another object of the invention to provide a dietary supplement obtained from the reaction product of sodium bicarbonate and raw apple cider vinegar solutions.

It is a further object of the invention to provide a dietary supplement obtained from lyophilization of the reaction product of sodium bicarbonate and raw apple cider vinegar solutions and packaging the resultant powder in gel capsules.

Still another object of the invention is to provide a dieatary supplement which is inexpensive and effective to improve digestion, rid blood impurities and relieves arthritic pain of humans.

It is an object of the invention to provide an improved dietary supplement thereof for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENT

The present invention is directed to an economical and easily produced dietary supplement for the relief of common human medical problems such as poor digestion, impure blood and arthritic pain.

A range of 2–4 oz. (avoirdupois) of baking soda or sodium bicarbonate is mixed with 30–40 fluid oz. of commercially available apple cider vinegar.

More specifically, 2.55 oz. (avoirdupois) of baking soda or sodium bicarbonate was added to 34 fluid oz. of raw apple cider vinegar originally at a pH of approximately 4 at room temperature. The final solution pH should be in the range of 9.0 to 10.0 and preferably 9. The aqueous reaction solution is lyophilized for at least 24 hours at a freezing temperature under a constant vacuum. The resulting fine powder is beige colored and placed in gelatin capsules for ingestion.

A gas mass spectrographic analysis has shown the following proportions of chemicals present in the liquid reaction product for a 16 fluid oz. sample: 28 mg. sodium, 237.5 mg. potassium, 14 mg. calcium, 21.5 mg. phosphorus, and 1.41 mg. iron.

The nutrient facts for the same quantity of the reaction solution are as follows: 33.63 calories, 14 gm. carbohydrate, a trace of protein, no fat, no fiber, no sugar, and the balance neutralized acetic acid salts.

The powder product has been treated with a dilute hydrochloric solution to bring the pH down to 4.0 to simulate the acid conditions of the stomach. The powder product has completely dissolved to release its efficacious properties. Persons receiving this economical dietary supplement product have benefitted in terms of improved digestion, the cleansing of impure blood and lessened arthritic pain.

It is to be understood that the present invention is not limited to the embodiment described above, but encompasses any and all embodiments within the scope of the following claims.

We claim:

1. A dietary supplement comprising:

a lyophilized reaction product of 2–4 oz. (avoirdupois) sodium bicarbonate and 30–40 fluid oz. raw apple cider vinegar.

2. The dietary supplement according to claim 1, wherein said lyophilized reaction product contains sodium, potassium, calcium, phosphorus, and iron as determined by gas mass spectrographic analysis.

3. The dietary supplement according to claim 1, wherein the lyophilized reaction product is a fine granulated powder.

4. The dietary supplement according to claim 1, wherein the lyophilized reaction product has a beige color.

5. The dietary supplement according to claim 1, wherein the lyophilized reaction product is packaged in gelatin capsules.

6. The dietary supplement according to claim 1, wherein 2.55 oz. of powdered sodium bicarbonate is combined with 34 fluid oz. of apple cider vinegar.

7. The dietary supplement according to claim 1, wherein the pH of the combined solution is adjusted to a range of 9.0 to 10.0.

8. The dietary supplement according to claim 1, wherein the reaction product is lyophilized for 24 hours.

9. The dietary supplement according to claim 1, wherein the reaction product when subjected to an acidified aqueous solution at a pH of 4.0 dissolves readily for release of its components.

10. The dietary supplement according to claim 1, wherein said lyophilized reaction product contains a small number of calories, a low quantity of carbohydrates, a trace of protein, and the balance being neutralized acetic acid salts, said reaction product being devoid of fat, fiber and sugar.

* * * * *